US008242337B1

(12) United States Patent
Henke et al.

(10) Patent No.: US 8,242,337 B1
(45) Date of Patent: Aug. 14, 2012

(54) MAIZE VARIETY HYBRID 10124870

(75) Inventors: Gary Edward Henke, Marshall, MO (US); David Walter Whitaker, Narvon, PA (US); Robert Alan Guse, Evansville, IN (US); Nancy Guse, legal representative, Evansville, IN (US)

(73) Assignee: Pioneer Hi Bred International Inc, Johnston, IA (US)

( * ) Notice: Subject to any disclaimer, the term of this patent is extended or adjusted under 35 U.S.C. 154(b) by 253 days.

(21) Appl. No.: 12/632,080

(22) Filed: Dec. 7, 2009

(51) Int. Cl.

| | |
|---|---|
| ***A01H 5/00*** | (2006.01) |
| ***A01H 5/10*** | (2006.01) |
| ***A01H 1/02*** | (2006.01) |
| ***C12N 15/82*** | (2006.01) |

(52) U.S. Cl. ..................... 800/320.1; 800/263; 800/264; 800/275; 800/281; 800/284; 800/299; 800/300.1

(58) Field of Classification Search ........................ None
See application file for complete search history.

(56) References Cited

U.S. PATENT DOCUMENTS

| | | | | |
|---|---|---|---|---|
| 6,995,304 | B1 * | 2/2006 | Hoffbeck | 800/320.1 |
| 7,572,963 | B1 * | 8/2009 | Hoffbeck | 800/320.1 |
| 7,820,893 | B1 * | 10/2010 | Hoffbeck | 800/320.1 |
| 7,902,432 | B1 | 3/2011 | Hoffbeck | |
| 8,039,716 | B1 * | 10/2011 | Fischer et al. | 800/320.1 |

OTHER PUBLICATIONS

Plant Variety Protection Certificate No. 200800338 for Corn PHGMA, filed Jul. 30, 2008.
Plant Variety Protection Certificate No. 200800343 for Corn PHNWJ, filed Jul. 30, 2008.
Plant Variety Protection Certificate No. 200800261 for Corn PHVAM, filed May 9, 2008.

* cited by examiner

*Primary Examiner* — David T Fox

(57) ABSTRACT

A novel maize variety designated 10124870 and seed, plants and plant parts thereof, produced by crossing Pioneer Hi-Bred International, Inc. proprietary inbred maize varieties. Methods for producing a maize plant that comprises crossing maize variety 10124870 with another maize plant. Methods for producing a maize plant containing in its genetic material one or more traits introgressed into 10124870 through back-cross conversion and/or transformation, and to the maize seed, plant and plant part produced thereby. This invention relates to the maize variety 10124870, the seed, the plant produced from the seed, and variants, mutants, and minor modifications of maize variety 10124870. This invention further relates to methods for producing maize varieties derived from maize variety 10124870.

20 Claims, No Drawings

MAIZE VARIETY HYBRID 10124870

FIELD OF THE INVENTION

This invention relates generally to the field of maize breeding, specifically relating to maize variety designated 10124870.

BACKGROUND OF THE INVENTION

The goal of hybrid development is to combine, in a single hybrid, various desirable traits. For field crops, these traits may include resistance to diseases and insects, resistance to heat and drought, reducing the time to crop maturity, greater yield, and better agronomic quality. With mechanical harvesting of many crops, uniformity of plant characteristics such as germination, stand establishment, growth rate, maturity, and plant and ear height is important. Traditional plant breeding is an important tool in developing new and improved commercial crops.

SUMMARY OF THE INVENTION

According to the invention, there is provided a maize variety, seed, plant, and its parts designated as 10124870, produced by crossing two Pioneer Hi-Bred International, Inc. proprietary maize inbred varieties. This invention relates to the maize variety 10124870, the seed, the plant and its parts produced from the seed, and variants, mutants and minor modifications of maize 10124870. This invention also relates to processes for making a maize plant containing in its genetic material one or more traits introgressed into 10124870 through locus conversion and/or transformation, and to the maize seed, plant and plant parts produced thereby. This invention further relates to methods for producing maize varieties derived from maize variety 10124870.

DEFINITIONS

Certain definitions used in the specification are provided below. Also in the examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit a trait. For example, STKLDG % NOT is the percentage of plants in a plot that were not stalk lodged. These designators will follow the descriptors to denote how the values are to be interpreted. Below are the descriptors used in the data tables included herein.

ABIOTIC STRESS TOLERANCE: Resistance to non-biological sources of stress conferred by traits such as nitrogen utilization efficiency, altered nitrogen responsiveness, drought resistance cold, and salt resistance.

ABTSTK=ARTIFICIAL BRITTLE STALK: A count of the number of "snapped" plants per plot following machine snapping. A snapped plant has its stalk completely snapped at a node between the base of the plant and the node above the ear. Expressed as percent of plants that did not snap.

ADF=PERCENT ACID DETERGENT FIBER: The percent of dry matter that is acid detergent fiber in chopped whole plant forage.

ALEURONE: A thin layer of cells just beneath the pericarp of the seed.

ALLELE: Any of one or more alternative forms of a genetic sequence. In a diploid cell or organism, the two alleles of a given sequence typically occupy corresponding loci on a pair of homologous chromosomes.

ALTER: The utilization of up-regulation, down-regulation, or gene silencing.

ANTHESIS: The time of a flower's opening.

ANTHOCYANIN OF BRACE ROOTS: The degree of red coloration of the brace roots after exposure to sunlight taken at flowering. Brace root anthocyanin is scored 1-5 where 1=no red color, 2=pink, 3=red, 4=dark red, and 5=purple.

ANTIOXIDANT: A chemical compound or substance that inhibits oxidation, including but not limited to tocopherol or tocotrienols.

ANT ROT=ANTHRACNOSE STALK ROT (*Colletotrichum graminicola*): A 1 to 9 visual rating indicating the resistance to Anthracnose Stalk Rot. A higher score indicates a higher resistance. Data are collected only when sufficient selection pressure exists in the experiment measured.

BACKCROSSING: Process in which a breeder crosses a progeny variety back to one of the parental genotypes one or more times.

BACKCROSS PROGENY: Progeny plants produced by crossing a maize inbred parent of 10124870 plant with maize plants that comprise desired traits or loci, selecting F1 progeny plants that comprise the desired traits or loci, and crossing the selected F1 progeny plants with the 10124870 plants 1 or more times to produce backcross progeny plants that comprise said traits or loci.

BAR GLUMES: (glume band) The presence or absence of horizontal lines at the base of the glumes on tassel florets.

BARPLT=BARREN PLANTS: The percent of plants per plot that were not barren, i.e., lack an ear with grain, or have an ear with only a few scattered kernels.

BORBMN=ARTIFICIAL BRITTLE STALK MEAN: The mean percent of plants not "snapped" in a plot following artificial selection pressure. A snapped plant has its stalk completely snapped at a node between the base of the plant and the node above the ear. Expressed as percent of plants that did not snap. A high number is good and indicates tolerance to brittle snapping.

BRANCH ANGLE FROM CENTRAL SPIKE: The adaxial angle measured in degrees with a protractor on the top primary lateral tassel branch at flowering.

BRENGMN=BRITTLE STALK ENERGY MEAN: The mean amount of energy per unit area needed to artificially brittle snap a corn stalk. A high number is good and indicates tolerance to brittle snapping.

BREEDING: The genetic manipulation of living organisms.

BREEDING CROSS: A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed.

BRLPNE=ARTIFICIAL ROOT LODGING EARLY SEASON: The percent of plants not root lodged in a plot following artificial selection pressure applied prior to flowering. A plant is considered root lodged if it leans from the vertical axis at an approximately 30 degree angle or greater. Expressed as percent of plants that did not root lodge. A high number is good and indicates tolerance to preflowering root lodging.

BRLPNL=ARTIFICIAL ROOT LODGING LATE SEASON: The percent of plants not root lodged in a plot following artificial selection pressure during grain fill. A plant is considered root lodged if it leans from the vertical axis at an approximately 30 degree angle or greater. Expressed as percent of plants that did not root lodge. A high number is good and indicates tolerance to late season root lodging.

BRTSTK=BRITTLE STALKS: This is a measure of the stalk breakage near the time of pollination, and is an indication of whether a hybrid or inbred would snap or break near the time of flowering under severe winds. Data are presented as percentage of plants that did not snap. Data are collected only when sufficient selection pressure exists in the experiment measured.

CARBOHYDRATE: Organic compounds comprising carbon, oxygen and hydrogen, including sugars, starches and cellulose.

CELL: Cell as used herein includes a plant cell, whether isolated, in tissue culture or incorporated in a plant or plant part.

CLDTST=COLD TEST: The percent of plants that germinate under cold test conditions.

CLN=CORN LETHAL NECROSIS: Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance. Data are collected only when sufficient selection pressure exists in the experiment measured.

COMRST=COMMON RUST (*Puccinia sorghi*): A 1 to 9 visual rating indicating the resistance to Common Rust. A higher score indicates a higher resistance. Data are collected only when sufficient selection pressure exists in the experiment measured.

COMMON SMUT (Ustilago maydis): A 1 to 9 visual rating indicating the resistance to Common Smut. A higher score indicates a higher resistance. Data is collected only when sufficient selection pressure exists in the experiment measured.

CP=PERCENT OF CRUDE PROTEIN: The percent of dry matter that is crude protein in chopped whole plant forage.

CROSS POLLINATION: A plant is cross pollinated if the pollen comes from a flower on a different plant from a different family or variety. Cross pollination excludes sib and self pollination.

CROSSING: The combination of genetic material by traditional methods such as a breeding cross or backcross, but also including protoplast fusion and other molecular biology methods of combining genetic material from two sources.

CRWNIS=CORN ROOTWORM NODE INJURY SCALE (*Diabrotica* sp.): A 0-3 visual rating based on the proportion of roots pruned by corn rootworm larvae to less than 1.5 inches of the crown. 0 indicates no feeding, 3 indicates a total of 3 entire nodes of roots pruned.

D/D=DRYDOWN: This represents the relative rate at which a variety will reach acceptable harvest moisture compared to other varieties on a 1 to 9 rating scale. A high score indicates a variety that dries relatively fast while a low score indicates a variety that dries slowly.

DIPERS=DIPLODIA EAR MOLD SCORES (*Diplodia maydis* and *Diplodia macrospora*): A 1 to 9 visual rating indicating the resistance to *Diplodia* Ear Mold. A higher score indicates a higher resistance. Data are collected only when sufficient selection pressure exists in the experiment measured.

DIPLOID PLANT PART: Refers to a plant part or cell that has the same diploid genotype as 10124870.

DIPROT=DIPLODIA STALK ROT SCORE: Score of stalk rot severity due to *Diplodia* (*Diplodia maydis*). Expressed as a 1 to 9 score with 9 being highly resistant. Data are collected only when sufficient selection pressure exists in the experiment measured.

DM=PERCENT OF DRY MATTER: The percent of dry material in chopped whole plant silage.

DRPEAR=DROPPED EARS: A measure of the number of dropped ears per plot and represents the percentage of plants that did not drop ears prior to harvest. Data are collected only when sufficient selection pressure exists in the experiment measured.

D/T=DROUGHT TOLERANCE: This represents a 1 to 9 rating for drought tolerance, and is based on data obtained under stress conditions. A high score indicates good drought tolerance and a low score indicates poor drought tolerance. Data are collected only when sufficient selection pressure exists in the experiment measured.

EARHT=EAR HEIGHT: The ear height is a measure from the ground to the highest placed developed ear node attachment and is measured in centimeters.

EARMLD=GENERAL EAR MOLD: Visual rating (1 to 9 score) where a 1 is very susceptible and a 9 is very resistant. This is based on overall rating for ear mold of mature ears without determining the specific mold organism, and may not be predictive for a specific ear mold. Data are collected only when sufficient selection pressure exists in the experiment measured.

EAR NODE: The node on the main stem that bears the top or primary ear.

EAR POSITION: The orientation of the primary ear 65 days after 50% silk. Ear position is scored as 1=upright, 2=horizontal, and 3=pendant (downward or drooping).

EAR SHANK LENGTH: The measurement of the structure from the butt of the primary ear to the ear node on the main stem.

EARSZ=EAR SIZE: A 1 to 9 visual rating of ear size. The higher the rating the larger the ear size.

EBTSTK=EARLY BRITTLE STALK: A count of the number of "snapped" plants per plot following severe winds when the corn plant is experiencing very rapid vegetative growth in the V5-V8 stage. Expressed as percent of plants that did not snap. Data are collected only when sufficient selection pressure exists in the experiment measured.

ECB1LF=EUROPEAN CORN BORER FIRST GENERATION LEAF

FEEDING (*Ostrinia nubilalis*): A 1 to 9 visual rating indicating the resistance to preflowering leaf feeding by first generation European Corn Borer. A higher score indicates a higher resistance. Data are collected only when sufficient selection pressure exists in the experiment measured.

ECB2IT=EUROPEAN CORN BORER SECOND GENERATION INCHES OF TUNNELING (*Ostrinia nubilalis*): Average inches of tunneling per plant in the stalk. Data are collected only when sufficient selection pressure exists in the experiment measured.

ECB2SC=EUROPEAN CORN BORER SECOND GENERATION (*Ostrinia nubilalis*): A 1 to 9 visual rating indicating post flowering degree of stalk breakage and other evidence of feeding by second generation European Corn Borer. A higher score indicates a higher resistance. Data are collected only when sufficient selection pressure exists in the experiment measured.

ECBDPE=EUROPEAN CORN BORER DROPPED EARS (*Ostrinia nubilalis*): propped ears due to European Corn Borer. Percentage of plants that did not drop ears under second generation European Corn Borer infestation. Data are collected only when sufficient selection pressure exists in the experiment measured.

ECBLSI=EUROPEAN CORN BORER LATE SEASON INTACT (*Ostrinia nubilalis*): A 1 to 9 visual rating indicating late season intactness of the corn plant given damage (stalk breakage above and below the top ear) caused primarily by $2^{nd}$ and/or $3^{rd}$ generation ECB larval feeding before harvest. A higher score is good and indicates more intact plants. Data are collected only when sufficient selection pressure exists in the experiment measured.

EGRWTH=EARLY GROWTH: This is a measure of the relative height and size of a corn seedling at the 2-4 leaf stage of growth. This is a visual rating (1 to 9), with 1 being weak or slow growth, 5 being average growth and 9 being strong growth. Taller plants, wider leaves, more green mass and darker color constitute a higher score. Data are collected only when sufficient selection pressure exists in the experiment measured.

ENDOSPERM: The nutritive tissue (starch) within the seed that surrounds the embryo.

ERTLDG=EARLY ROOT LODGING: The percentage of plants that do not root lodge prior to or around anthesis; plants that lean from the vertical axis at an approximately 30 degree angle or greater would be counted as root lodged. Data are collected only when sufficient selection pressure exists in the experiment measured.

ERTLPN=EARLY ROOT LODGING: An estimate of the percentage of plants that do not root lodge prior to or around anthesis; plants that lean from the vertical axis at an approximately 30 degree angle or greater would be considered as root lodged. Data are collected only when sufficient selection pressure exists in the experiment measured.

ERTLSC=EARLY ROOT LODGING SCORE: Score for severity of plants that lean from a vertical axis at an approximate 30 degree angle or greater which typically results from strong winds prior to or around flowering recorded within 2 weeks of a wind event. Expressed as a 1 to 9 score with 9 being no lodging. Data are collected only when sufficient selection pressure exists in the experiment measured.

ESSENTIAL AMINO ACIDS: Amino acids that cannot be synthesized de novo by an organism and therefore must be supplied in the diet.

ESTCNT=EARLY STAND COUNT: This is a measure of the stand establishment in the spring and represents the number of plants that emerge on a per plot basis for the inbred or hybrid.

EYESPT=EYE SPOT (*Kabatiella zeae* or *Aureobasidium zeae*): A 1 to 9 visual rating indicating the resistance to Eye Spot. A higher score indicates a higher resistance. Data are collected only when sufficient selection pressure exists in the experiment measured.

EXPRESSING: Having the genetic potential such that under the right conditions, the phenotypic trait is present.

FATTY ACID: A carboxylic acid (or organic acid), often with a long aliphatic tail (long chains), either saturated or unsaturated.

F1 PROGENY: A progeny plant produced by crossing a plant of maize variety 10124870 with a plant of another maize line.

FUSERS=FUSARIUM EAR ROT SCORE (*Fusarium moniliforme* or *Fusarium subglutinans*): A 1 to 9 visual rating indicating the resistance to *Fusarium Ear Rot. A higher score indicates a higher resistance. Data are collected only when sufficient selection pressure exists in the experiment measured.*

GDU=Growing Degree Units: Using the Barger Heat Unit Theory, which assumes that maize growth occurs in the temperature range 50 degrees F.-86 degrees F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=GDU TO SHED: The number of growing degree units (GDUs) or heat units required for an inbred variety or hybrid variety to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86 degrees F. and the lowest minimum temperature used is 50 degrees F. For each inbred or hybrid it takes a certain number of GDUs to reach various stages of plant development.

GDUSLK=GDU TO SILK: The number of growing degree units required for an inbred variety or hybrid variety to have approximately 50 percent of the plants with silk emergence from time of planting. Growing degree units are calculated by the Barger Method as given in GDU SHD definition.

GENE SILENCING: The interruption or suppression of the expression of a gene at the level of transcription or translation.

GENOTYPE: Refers to the genetic constitution of a cell or organism.

GIBERS=GIBBERELLA EAR ROT (PINK MOLD) (*Gibberella zeae*): A 1 to 9 visual rating indicating the resistance to *Gibberella* Ear Rot. A higher score indicates a higher resistance. Data are collected only when sufficient selection pressure exists in the experiment measured.

GIBROT=GIBBERELLA STALK ROT SCORE: Score of stalk rot severity due to *Gibberella* (*Gibberella zeae*). Expressed as a 1 to 9 score with 9 being highly resistant. Data are collected only when sufficient selection pressure exists in the experiment measured.

GLFSPT=GRAY LEAF SPOT (*Cercospora zeae-maydis*): A 1 to 9 visual rating indicating the resistance to Gray Leaf Spot. A higher score indicates a higher resistance. Data are collected only when sufficient selection pressure exists in the experiment measured.

GOSWLT=GOSS' WILT (*Corynebacterium nebraskense*): A 1 to 9 visual rating indicating the resistance to Goss' Wilt. A higher score indicates a higher resistance. Data are collected only when sufficient selection pressure exists in the experiment measured.

GRNAPP=GRAIN APPEARANCE: This is a 1 to 9 rating for the general appearance of the shelled grain as it is harvested based on such factors as the color of harvested grain, any mold on the grain, and any cracked grain. High scores indicate good grain quality.

H/POP=YIELD AT HIGH DENSITY: Yield ability at relatively high plant densities on a 1 to 9 relative rating system with a higher number indicating the variety responds well to high plant densities for yield relative to other varieties. A 1, 5, and 9 would represent very poor, average, and very good yield response, respectively, to increased plant density.

HAPLOID PLANT PART: Refers to a plant part or cell that has the same haploid genotype as 10124870.

HCBLT=HELMINTHOSPORIUM CARBONUM LEAF BLIGHT (*Helminthosporium carbonum*). A 1 to 9 visual rating indicating the resistance to *Helminthosporium* infection. A higher score indicates a higher resistance. Data are collected only when sufficient selection pressure exists in the experiment measured.

HD SMT=HEAD SMUT (*Sphacelotheca reiliana*): This score indicates the percentage of plants not infected. Data are collected only when sufficient selection pressure exists in the experiment measured.

HSKCVR=HUSK COVER: A 1 to 9 score based on performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

HUSK EXTENSION: The distance the husk extends past the end of the primary ear at harvest.

HUSK TIGHTNESS: The tightness of the husk 65 days after 50% silking on a scale from 1 (very loose) to 9 (very tight).

HYBRID VARIETY: A substantially heterozygous hybrid line and minor genetic modifications thereof that retain the overall genetics of the hybrid line including but not limited to a locus conversion, a mutation, or a somoclonal variant.

INBRED: A variety developed through inbreeding or doubled haploidy that preferably comprises homozygous alleles at about 95% or more of its loci.

INBRED VARIETY: A substantially homozygous inbred line and minor modifications thereof that retain the overall genetics of the inbred line including but not limited to a locus conversion, a mutation, or a somoclonal variant.

INC D/A=GROSS INCOME (DOLLARS PER ACRE): Relative income per acre assuming drying costs of two cents per point above 15.5 percent harvest moisture and current market price per bushel.

INCOME/ACRE: Income advantage of variety to be patented over other variety on per acre basis.

INC ADV=GROSS INCOME ADVANTAGE: Gross income advantage of variety #1 over variety #2.

INTERNODE: The structure between two nodes on the main stem.

INTROGRESSION: The process of transferring genetic material from one genotype to another.

KERUNT=KERNELS PER UNIT AREA: (Acres or Hectares).

KERPOP=KERNEL POP SCORE: The visual 1-9 rating of the amount of rupturing of the kernel pericarp at an early stage in grain fill. A higher score is good and indicates no popped (ruptured) kernels.

KER WT=KERNEL NUMBER PER UNIT WEIGHT: (Pounds or Kilograms). The number of kernels in a specific measured weight; determined after removal of extremely small and large kernels.

KSZDCD=KERNEL SIZE DISCARD: The percent of discard seed; calculated as the sum of discarded tip kernels and extra large kernels.

LEAF ANGLE: The adaxial angle measured in degrees with a protractor on the second leaf above the top ear at flowering.

LEAF SHEATH PUBESCENCE: The density of pubescence on the face of the leaf sheath at flowering. Leaf Sheath Pubescence is scored on a 1-9 scale where 1=no pubescence (smooth) and 9=high level of pubescence (like peach fuzz).

LINKAGE: Refers to a phenomenon wherein alleles on the same chromosome tend to segregate together more often than expected by chance if their transmission was independent.

LINKAGE DISEQUILIBRIUM: Refers to a phenomenon wherein alleles tend to remain together in linkage groups when segregating from parents to offspring, with a greater frequency than expected from their individual frequencies.

LOCUS: A specific location on a chromosome.

LOCUS CONVERSION: A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single corn variety.

L/POP=YIELD AT LOW DENSITY: Yield ability at relatively low plant densities on a 1 to 9 relative system with a higher number indicating the variety responds well to low plant densities for yield relative to other varieties. A 1, 5, and 9 would represent very poor, average, and very good yield response, respectively, to low plant density.

LRTLDG=LATE ROOT LODGING: The percentage of plants that do not root lodge after anthesis through harvest; plants that lean from the vertical axis at an approximately 30 degree angle or greater would be counted as root lodged. Data are collected only when sufficient selection pressure exists in the experiment measured.

LRTLPN=LATE ROOT LODGING: An estimate of the percentage of plants that do not root lodge after anthesis through harvest; plants that lean from the vertical axis at an approximately 30 degree angle or greater would be considered as root lodged. Data are collected only when sufficient selection pressure exists in the experiment measured.

LRTLSC=LATE ROOT LODGING SCORE: Score for severity of plants that lean from a vertical axis at an approximate 30 degree angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging. Data are collected only when sufficient selection pressure exists in the experiment measured.

MALE STERILITY: A male sterile plant is one which produces no viable pollen. Male sterility prevents self pollination and the pollination of neighboring plants. These male sterile plants are therefore useful in hybrid plant production.

MDMCPX=MAIZE DWARF MOSAIC COMPLEX (MDMV=Maize Dwarf Mosaic Virus and MCDV=Maize Chlorotic Dwarf Virus): A 1 to 9 visual rating indicating the resistance to Maize Dwarf Mosaic Complex. A higher score indicates a higher resistance. Data are collected only when sufficient selection pressure exists in the experiment measured.

MST=HARVEST MOISTURE: The moisture is the actual percentage moisture of the grain at harvest.

MSTADV=MOISTURE ADVANTAGE: The moisture advantage of variety #1 over variety #2 as calculated by: MOISTURE of variety #2−MOISTURE of variety #1=MOISTURE ADVANTAGE of variety #1.

NEI DISTANCE: A quantitative measure of percent similarity between two varieties. Nei's distance between varieties A and B can be defined as 1−(2*number alleles in common/(number alleles in A+number alleles in B). For example, if lines A and B are the same for 95 out of 100 alleles, the Nei distance would be 0.05. If varieties A and B are the same for 98 out of 100 alleles, the Nei distance would be 0.02. Free software for calculating Nei distance is available on the internet at multiple locations such as, for example, at: evolution.genetics.washington.edu/phylip.html. See Nei, Proc Natl Acad Sci, 76:5269-5273 (1979) which is incorporated by reference for this purpose.

NLFBLT=NORTHERN LEAF BLIGHT (*Helminthosporium turcicum* or *Exserohilum turcicum*): A 1 to 9 visual rating indicating the resistance to Northern Leaf Blight. A higher score indicates a higher resistance. Data are collected only when sufficient selection pressure exists in the experiment measured.

NUCLEIC ACID: An acidic, chainlike biological macromolecule consisting of multiple repeat units of phosphoric acid, sugar and purine and pyrimidine bases.

OILT=GRAIN OIL: Absolute value of oil content of the kernel as predicted by Near-Infrared Transmittance and expressed as a percent of dry matter.

PEDUNCLE NODE: The node on the main stem that the tassel originates from.

PERCENT IDENTITY: Percent identity as used herein refers to the comparison of the alleles of two plants or varieties as scored by matching loci. Percent identity is determined by comparing a statistically significant number of the loci of two plants or varieties and scoring a match when the same two alleles are present at the same loci for each plant. For example, a percent identity of 90% between maize variety 10124870 and another plant means that the two plants have the same two alleles at 90% of their loci.

PLANT: As used herein, the term "plant" includes reference to an immature or mature whole plant, including a plant that has been detasseled or from which seed or grain has been removed. Seed or embryo that will produce the plant is also considered to be the plant.

PLANT PART: As used herein, the term "plant part" includes leaves, stems, roots, seed, grain, embryo, pollen, ovules, flowers, ears, cobs, husks, stalks, root tips, anthers, pericarp, silk, tissue, cells and the like.

PLTHT=PLANT HEIGHT: This is a measure of the height of the plant from the ground to the tip of the tassel in centimeters.

POLPRD=POLLEN PRODUCTION SCORE: The estimated total amount of pollen produced by tassels based on the number of tassel branches and the density of the spikelets.

POLSC=POLLEN SCORE: A 1 to 9 visual rating indicating the amount of pollen shed. The higher the score the more pollen shed.

POLWT=POLLEN WEIGHT: This is calculated by dry weight of tassels collected as shedding commences minus dry weight from similar tassels harvested after shedding is complete.

POP K/A=PLANT POPULATIONS: Measured as 1000's per acre.

POP ADV=PLANT POPULATION ADVANTAGE: The plant population advantage of variety #1 over variety #2 as calculated by PLANT POPULATION of variety #2−PLANT POPULATION of variety #1=PLANT POPULATION ADVANTAGE of variety #1.

PRM=PREDICTED RELATIVE MATURITY: This trait, predicted relative maturity, is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PRMSHD: A relative measure of the growing degree units (GDU) required to reach 50% pollen shed. Relative values are predicted values from the linear regression of observed GDU's on relative maturity of commercial checks.

PRIMARY LATERAL TASSEL BRANCH: A branch that originates off the main axis of the tassel with more than 2 florets.

PROT=GRAIN PROTEIN: Absolute value of protein content of the kernel as predicted by Near-Infrared Transmittance and expressed as a percent of dry matter.

RESISTANCE: Synonymous with tolerance. The ability of a plant to withstand exposure to an insect, disease, herbicide or other condition. A resistant plant variety will have a level of resistance higher than a comparable wild-type variety.

RTLDG=ROOT LODGING: Root lodging is the percentage of plants that do not root lodge; plants that lean from the vertical axis at an approximately 30 degree angle or greater would be counted as root lodged. Data are collected only when sufficient selection pressure exists in the experiment measured.

RTLADV=ROOT LODGING ADVANTAGE: The root lodging advantage of variety #1 over variety #2. Data are collected only when sufficient selection pressure exists in the experiment measured.

SCTGRN=SCATTER GRAIN: A 1 to 9 visual rating indicating the amount of scatter grain (lack of pollination or kernel abortion) on the ear. The higher the score the less scatter grain.

SDGVGR=SEEDLING VIGOR: This is the visual rating (1 to 9) of the amount of vegetative growth after emergence at the seedling stage (approximately five leaves). A higher score indicates better vigor.

SEED: Fertilized and ripened ovule, consisting of the plant embryo, varying amounts of stored food material, and a protective outer seed coat. Synonymous with grain.

SEL IND=SELECTION INDEX: The selection index gives a single measure of the maize variety's worth based on information for multiple traits. A maize breeder may utilize his or her own set of traits for the selection index. One of the traits that is almost always included is yield. The selection index data presented in the tables represent the mean value averaged across testing stations.

SIL DMP=SILAGE DRY MATTER: The percent of dry material in chopped whole plant silage.

SELF POLLINATION: A plant is self-pollinated if pollen from one flower is transferred to the same or another flower of the same plant.

SIB POLLINATION: A plant is sib-pollinated when individuals within the same family or variety are used for pollination.

SITE SPECIFIC INTEGRATION: Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821.

SLFBLT=SOUTHERN LEAF BLIGHT (*Helminthosporium maydis* or *Bipolaris maydis*): A 1 to 9 visual rating indicating the resistance to Southern Leaf Blight. A higher score indicates a higher resistance. Data are collected only when sufficient selection pressure exists in the experiment measured.

SOURST=SOUTHERN RUST (*Puccinia polysora*): A 1 to 9 visual rating indicating the resistance to Southern Rust. A higher score indicates a higher resistance. Data are collected only when sufficient selection pressure exists in the experiment measured.

SPKDSC=SPIKLET DENSITY SCORE: The visual 1-9 rating of how dense spikelets are on the middle tassel branches. A higher score indicates higher spikelet density.

STAGRN=STAY GREEN: Stay green is the measure of plant health near the time of black layer formation (physiological maturity). A high score indicates better late-season plant health.

STARCH=PERCENT OF STARCH: The percent of dry matter that is starch in chopped whole plant forage.

STDADV=STALK STANDING ADVANTAGE: The advantage of variety #1 over variety #2 for the trait STK CNT.

STKCNT=NUMBER OF PLANTS: This is the final stand or number of plants per plot.

STKLDG=STALK LODGING REGULAR: This is the percentage of plants that did not stalk lodge (stalk breakage) at regular harvest (when grain moisture is between about 20 and 30%) as measured by either natural lodging or pushing the stalks and determining the percentage of plants that break below the ear. Data are collected only when sufficient selection pressure exists in the experiment measured.

STKLDS=STALK LODGING SCORE: A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging. Data are collected only when sufficient selection pressure exists in the experiment measured.

STLLPN=LATE STALK LODGING: This is the percent of plants that did not stalk lodge (stalk breakage or crimping) at or around late season harvest (when grain moisture is below 20%) as measured by either natural lodging or pushing the stalks and determining the percentage of plants that break or crimp below the ear. Data are collected only when sufficient selection pressure exists in the experiment measured.

STLPCN=STALK LODGING REGULAR: This is an estimate of the percentage of plants that did not stalk lodge (stalk breakage) at regular harvest (when grain moisture is between about 20 and 30%) as measured by either natural lodging or pushing the stalks and determining the percentage of plants that break below the ear. Data are collected only when sufficient selection pressure exists in the experiment measured.

STLTIP=STERILE TIPS SCORE: The visual 1 to 9 rating of the relative lack of glumes on the tassel central spike and branches. A higher score indicates less incidence of sterile tips or lack of glumes on the tassel.

STRT=GRAIN STARCH: Absolute value of starch content of the kernel as predicted by Near-Infrared Transmittance and expressed as a percent of dry matter.

STWWLT=Stewart's Wilt (*Erwinia stewartii*): A 1 to 9 visual rating indicating the resistance to Stewart's Wilt. A higher score indicates a higher resistance. Data are collected only when sufficient selection pressure exists in the experiment measured.

SSRs: Genetic markers based on polymorphisms in repeated nucleotide sequences, such as microsatellites. A marker system based on SSRs can be highly informative in linkage analysis relative to other marker systems in that multiple alleles may be present.

TASBLS=TASSEL BLAST: A 1 to 9 visual rating was used to measure the degree of blasting (necrosis due to heat stress) of the tassel at the time of flowering. A 1 would indicate a very high level of blasting at time of flowering, while a 9 would have no tassel blasting. Data are collected only when sufficient selection pressure exists in the experiment measured.

TASBRN=TASSEL BRANCH NUMBER: The number of tassel branches, with anthers originating from the central spike.

TASSZ=TASSEL SIZE: A 1 to 9 visual rating was used to indicate the relative size of the tassel. The higher the rating the larger the tassel.

TAS WT=TASSEL WEIGHT: This is the average weight of a tassel (grams) just prior to pollen shed.

TDM/HA=TOTAL DRY MATTER PER HECTARE: Yield of total dry plant material in metric tons per hectare.

TEXEAR=EAR TEXTURE: A 1 to 9 visual rating was used to indicate the relative hardness (smoothness of crown) of mature grain. A 1 would be very soft (extreme dent) while a 9 would be very hard (flinty or very smooth crown).

TILLER=TILLERS: A count of the number of tillers per plot that could possibly shed pollen was taken. Data are given as a percentage of tillers: number of tillers per plot divided by number of plants per plot. A tiller is defied as a secondary shoot that has developed as a tassel capable of shedding pollen.

TST WT=TEST WEIGHT (UNADJUSTED): The measure of the weight of the grain in kilograms for a given volume (cubic meter).

TSWADV=TEST WEIGHT ADVANTAGE: The test weight advantage of variety #1 over variety #2.

TOP EAR: The highest and primary seed bearing structure of the corn plant.

WIN M %=PERCENT MOISTURE WINS:

WIN Y %=PERCENT YIELD WINS:

YIELD BU/A=YIELD (BUSHELS/ACRE): Yield of the grain at harvest in bushels per acre adjusted to 15% moisture.

YLDADV=YIELD ADVANTAGE: The yield advantage of variety #1 over variety #2 as calculated by: YIELD of variety #1−YIELD variety #2=YIELD ADVANTAGE of variety #1.

YLDSC=YIELD SCORE: A 1 to 9 visual rating was used to give a relative rating for yield based on plot ear piles. The higher the rating the greater visual yield appearance.

When referring to area of adaptability, such term is used to describe the location with the environmental conditions that would be well suited for this maize variety. Area of adaptability is based on a number of factors, for example: days to maturity, insect resistance, disease resistance, and drought resistance. Area of adaptability does not indicate that the maize variety will grow in every location within the area of adaptability or that it will not grow outside the area.

DETAILED DESCRIPTION OF THE INVENTION AND FURTHER EMBODIMENTS

All tables discussed in the Detailed Description of the Invention and Further Embodiments section can be found at the end of the section.

Field crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

Maize (*Zea mays* L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

There are many important factors to be considered in the art of plant breeding, such as the ability to recognize important characteristics, the ability to design evaluation techniques for genotypic and phenotypic traits of interest, and the ability to search out and exploit the genes for the desired traits in new or improved combinations.

One objective of commercial maize variety development is to produce hybrids with high grain yields and superior agronomic performance. One of the primary traits breeders seek is yield. However, many other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance.

Phenotypic Characteristics of 10124870

Pioneer Brand Maize Variety 10124870 is a single cross, yellow endosperm maize variety. Maize Variety 10124870 has a relative maturity of approximately 112 based on the Comparative Relative Maturity Rating System for harvest moisture of grain. Maize Variety 10124870 is characterized by excellent yield its maturity adapted to the Central and Eastern Corn Belt. In addition, Maize Variety 10124870 has outstanding root strength, above average plant height/ear placement and good Northern Leaf Blight resistance.

The maize variety has shown uniformity and stability within the limits of environmental influence for all the traits as described in the Variety Description Information (Table 1, found at the end of the section). The inbred parents of this maize variety have been self-pollinated and ear-rowed a sufficient number of generations with careful attention paid to uniformity of plant type to ensure the homozygosity and phenotypic stability necessary for use in commercial hybrid seed production. The variety has been increased both by hand and in isolated fields with continued observation for uniformity. No variant traits have been observed or are expected in 10124870.

Maize variety 10124870 can be reproduced by planting seeds of the inbred parent varieties, growing the resulting maize plants under cross pollinating conditions, and harvesting the resulting seed using techniques familiar to the agricultural arts.

Genotypic Characteristics of 10124870

In addition to phenotypic observations, a plant can also be described by its genotype. The genotype of a plant can be characterized through a genetic marker profile. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don, et al., "Assessing Probability of Ancestry Using Simple Sequence Repeat Profiles: Applications to Maize Hybrids and Inbreds", Genetics, 2002, 161: 813-824, and Berry, Don et al., "Assessing Probability of Ancestry Using Simple Sequence Repeat Profiles: Applications to Maize Inbred Lines and Soybean Varieties", Genetics, 2003, 165: 331-342, which are incorporated by reference herein in their entirety.

Particular markers used for these purposes may include any type of marker and marker profile which provides a means of distinguishing varieties. In addition to being used for identification of maize variety 10124870 and its plant parts, the genetic marker profile is also useful in developing a locus conversion of 10124870.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR™ detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by gel electrophoresis of the amplification products. Scoring of marker genotype is based on the size of the amplified fragment, which may be measured by the base pair weight or molecular weight of the fragment. While variation in the primer used or in laboratory procedures can affect the reported molecular weight, relative values should remain constant regardless of the specific primer or laboratory used. When comparing plants it is preferable if all SSR profiles are performed in the same lab. An SSR service is available to the public on a contractual basis by DNA Landmarks in Saint-Jean-sur-Richelieu, Quebec, Canada.

Primers used for SSRs are publicly available and may be found in the Maize GDB on the World Wide Web at maizegdb.org (sponsored by the USDA Agricultural Research Service), in Sharopova et al. (Plant Mol. Biol. 48 (5-6):463-481), Lee et al. (Plant Mol. Biol. 48 (5-6); 453-461). Primers may be constructed from publicly available sequence information. Some marker information may be available from DNA Landmarks.

Comparisons of Pioneer Maize Variety 10124870

In addition to knowledge of the germplasm and plant genetics, a part of the hybrid selection process is dependent on experimental design coupled with the use of statistical analysis. Experimental design and statistical analysis are used to help determine which hybrid combinations are significantly better or different for one or more traits of interest. Experimental design methods are used to assess error so that differences between two hybrid varieties can be more accurately evaluated. Statistical analysis includes the calculation of mean values, determination of the statistical significance of the sources of variation, and the calculation of the appropriate variance components. One of ordinary skill in the art of plant breeding would know how to evaluate the traits of two plant varieties to determine if there is no significant difference between the two traits expressed by those varieties. For example, see Fehr, Walt, Principles of Cultivar Development, pages 261-286 (1987). Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide, insect or disease resistance. For example, a locus conversion of 10124870 for herbicide resistance should be compared with an isogenic counterpart in the absence of the herbicide.

In Table 2 (Table 2, found at the end of the section), data from traits and characteristics of maize variety 10124870 per se are given and compared to other maize varieties. The results in Table 2 show maize variety 10124870 has significantly different traits compared to other maize varieties (Mean1=Mean of Variety 1, Mean2=Mean of Variety 2, Locs=the number of locations used for statistics reported in the table, Reps=the number of replications used for statistics reported in the table, Diff=difference between the means, Prob=probability of significant difference between means, in general one may use probability of less than or equal to 0.10 or less than or equal to 0.05 to determine a statistical significant difference between means).

Development of Maize Hybrids using 10124870

During the inbreeding process in maize, the vigor of the varieties decreases. However, vigor is restored when two different inbred varieties are crossed to produce the hybrid progeny (F1). An important consequence of the homozygosity and homogeneity of the inbred varieties is that the hybrid between a defined pair of inbreds may be reproduced indefinitely as long as the homogeneity of the inbred parents is maintained. Once the inbreds that create a superior hybrid have been identified, a continual supply of the hybrid seed can be produced using these inbred parents and the hybrid corn plants can then be generated from this hybrid seed supply.

10124870 may also be used to produce a double cross hybrid or a three-way hybrid. A single cross hybrid is produced when two inbred varieties are crossed to produce the F1 progeny. A double cross hybrid is produced from four inbred varieties crossed in pairs (A×B and C×D) and then the two F1 hybrids are crossed again (A×B)×(C×D). A three-way cross hybrid is produced from three inbred varieties where two of the inbred varieties are crossed (A×B) and then the resulting F1 hybrid is crossed with the third inbred variety (A×B)×C. In each case, pericarp tissue from the female parent will be a part of and protect the hybrid seed.

Another form of commercial hybrid production involves the use of a mixture of male sterile hybrid seed and male pollinator seed. When planted, the resulting male sterile hybrid plants are pollinated by the pollinator plants. This method is primarily used to produce grain with enhanced quality grain traits, such as high oil, because desired quality grain traits expressed in the pollinator will also be expressed in the grain produced on the male sterile hybrid plant. In this method the desired quality grain trait does not have to be incorporated by lengthy procedures such as recurrent backcross selection into an inbred parent line. One use of this method is described in U.S. Pat. Nos. 5,704,160 and 5,706,603.

Locus Conversions of Maize Variety 10124870

10124870 represents a new base genetic line into which a new locus or trait may be introduced. Direct transformation and backcrossing represent two important methods that can be used to accomplish such an introgression. The term locus conversion is used to designate the product of such an introgression.

To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Once such a variety is developed its value to society is substantial since it is important to advance the germplasm base as a whole in order to maintain or improve traits such as yield, disease resistance, pest resistance and plant performance in extreme weather conditions. Locus conversions are routinely used to add or modify one or a few traits of such a line and this further enhances its value and usefulness to society.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of 10124870 may be characterized as having essentially the same phenotypic traits as 10124870. The traits used for comparison may be those traits shown in Table 1 or Table 2. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A locus conversion of 10124870 will retain the genetic integrity of 10124870. A locus conversion of 10124870 will comprise at least 92%, 93%, 94%, 95%, 96%, 97%, 98% or 99% of the base genetics of 10124870. For example, a locus conversion of 10124870 can be developed when DNA sequences are introduced through backcrossing (Hallauer et al., 1988), with a parent of 10124870 utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single locus traits that are relatively easy to classify, the backcross method is effective and relatively easy to manage. (See Hallauer et al. in Corn and Corn Improvement, Sprague and Dudley, Third Ed. 1998). Desired traits that may be transferred through locus conversion include, but are not limited to, waxy starch, sterility (nuclear and cytoplasmic), fertility restoration, grain color (white), drought resistance enhanced nitrogen utilization efficiency, altered nitrogen responsiveness, altered fatty acid profile, disease resistance (bacterial, fungal or viral), insect resistance, herbicide resistance and yield enhancements. In addition, an introgression site itself, such as an FRT site, Lox site or other site specific integration site, may be inserted by backcrossing and utilized for direct insertion of one or more genes of interest into a specific plant variety. The trait of interest is transferred from the donor parent to the recurrent parent, in this case, an inbred parent of the maize variety disclosed herein.

The seed industry commonly markets "triple stacks" of base genetics; which can be varieties comprising a locus conversion of at least 3 loci. Similarly, "quadruple stacks" would comprise the base genetics and could comprise a locus conversion of at least 4 loci. Stacking of traits is common to those of ordinary skill in the art of plant breeding and stacked traits account for a significant percentage of commercial corn hybrid sales. For example, figures from Purdue University show that biotech-trait corn accounted for 61% of all corn acres in 2006 and corn with two or more stacked traits accounted for 11.9 million acres. That's a significant portion of the approximately 80 million acres of corn grown in the United States. In addition, for 2007 at least one company projects selling more triple-stack corn hybrids than single trait hybrids. (Wayne Wenzel, "Double, Triple, Quad", published Nov. 8, 2006, Agweb.com, accessed Dec. 4, 2006). A single locus may contain several transgenes, such as a transgene for disease resistance that, in the same expression vector, also contains a transgene for herbicide resistance. As used herein, the phrase 'comprising a' transgene, transgenic event or locus conversion means one or more transgenes, transgenic events or locus conversions. The gene for herbicide resistance may be used as a selectable marker and/or as a phenotypic trait. A locus trait conversion of a site specific integration system allows for the integration of multiple genes at the converted loci. Further, SSI and FRT technologies known to those of skill in the art in the art may result in multiple gene introgressions at a single locus.

The locus conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype and/or genotype of the recurrent parent. While occasionally additional polynucleotide sequences or genes may be transferred along with the backcross conversion, the backcross conversion variety "fits into the same hybrid combination as the recurrent parent inbred variety and contributes the effect of the additional gene added through the backcross." See Poehlman et al. (1995, page 334). It has been proposed that in general there should be at least four backcrosses when it is important that the recovered varieties be essentially identical to the recurrent parent except for the characteristic being transferred (Fehr 1987, Principles of Cultivar Development). However, as noted above, the number of backcrosses necessary can be reduced with the use of molecular markers. Other factors, such as a genetically similar donor parent, may also reduce the number of backcrosses necessary.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. All of such embodiments are within the scope of the present claims. The term manipulated to be male sterile refers to the use of any available techniques to produce a male sterile version of maize variety 10124870. The male sterility may be either partial or complete male sterility.

Hybrid maize seed is often produced by a male sterility system incorporating manual or mechanical detasseling. Alternate strips of two inbred varieties of maize are planted in a field, and the pollen-bearing tassels are removed from one of the inbreds (female) prior to pollen shed. Providing that there is sufficient isolation from sources of foreign maize pollen, the ears of the detasseled inbred will be fertilized only from the other inbred (male), and the resulting seed is therefore hybrid and will form hybrid plants.

Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several ways in which a maize plant can be manipulated so that is male sterile. These include use of manual or mechanical emasculation (or detasseling), cytoplasmic genetic male sterility, nuclear genetic male sterility, gametocides and the like.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system can be blended to insure that adequate pollen loads are available for fertilization when the hybrid plants are grown. CMS systems have been successfully used since the 1950's, and the male sterility trait is routinely backcrossed into inbred varieties. See Wych, p. 585-586, 1998.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et al. EPO 89/3010153.8 Publication No. 329, 308 and PCT Application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

Transformation

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are stably inserted into the cell using transformation are referred to herein collectively as "transgenes" and/or "transgenic events". In some embodiments of the invention, a transformed variant of 10124870 may comprise at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transformed versions of the claimed maize variety 10124870 as well as combinations thereof.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been stably engineered into the germ cell line of a particular maize plant using transformation techniques, could be moved into the germ cell line of another variety using traditional breeding techniques that are well known in the plant breeding arts. These varieties can then be crossed to generate a hybrid maize variety plant such as maize variety plant 10124870 which comprises a transgenic event. For example, a backcrossing approach is commonly used to move a transgenic event from a transformed maize plant to another variety, and the resulting progeny would then comprise the transgenic event(s). Also, if an inbred variety was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953, which are herein incorporated by reference. In addition, transformability of a variety can be increased by introgressing the trait of high transformability from another variety known to have high transformability, such as Hi-II. See U.S. Patent Application Publication No. 2004/0016030.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92-6 (1981).

Transgenic events can be mapped by one of ordinary skill in the art and such techniques are well known to those of ordinary skill in the art. For exemplary methodologies in this regard, see for example, Glick and Thompson, Methods In Plant Molecular Biology And Biotechnology, 269-284 (CRC Press, Boca Raton, 1993).

Likewise, by means of the present invention, plants can be genetically engineered to express various phenotypes of agronomic interest. Through the transformation of maize the expression of genes can be altered to enhance disease resistance, insect resistance, herbicide resistance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) Plant Cell 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*), McDowell & Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other non-limiting examples of *Bacillus thuringiensis* transgenes being genetically engineered are given in the following patents and patent applications and hereby are incorporated by reference for this purpose: 5,188,960; 5,689,052; 5,880,275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018,615; 11/404,297; 11/404,638; 11/471,878; 11/780,501; 11/780,511; 11/780,503; 11/953,648; 11/953,648; and 11/957,893.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, and U.S. Pat. Nos. 6,563,020; 7,145,060 and 7,087,810.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al.,

*Plant Sci.* 89: 43 (1993), of heterologous expression of a cecropin-beta lytic peptide analog to render transgenic tobacco plants resistant to *Pseudomonas solanacearum.*

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5 (2) (1995), Pieterse & Van Loon (2004) Curr. Opin. Plant Bio. 7(4):456-64 and Somssich (2003) Cell 113(7):815-6.

(P) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. Nos. 09/950,933; 11/619,645; 11/657,710; 11/748,994; 11/774,121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716,820; 5,792,931; 5,798,255; 5,846,812; 6,083,736; 6,538,177; 6,388,171 and 6,812,380.

(R) Cystatin and cysteine proteinase inhibitors. See U.S. Pat. No. 7,205,453.

(S) Defensin genes. See WO03000863 and U.S. Pat. Nos. 6,911,577; 6,855,865; 6,777,592 and 7,238,781.

(T) Genes conferring resistance to nematodes. See e.g. PCT Application WO96/30517; PCT Application WO93/19181, WO 03/033651 and Urwin et al., Planta 204:472-479 (1998), Williamson (1999) Curr Opin Plant Bio. 2(4):327-31; and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent publication US20090035765 and incorporated by reference for this purpose. This includes the Rcg locus that may be utilized as a single locus conversion.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; U.S. application Ser. No. 11/683,737, and international publication WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. 10/427,692; 10/835,615 and 11/507,751. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer resistance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such As:

(A) Altered fatty acids, for example, by (1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superal1, mi1 ps, various Ipa genes such as Ipa1, Ipa3, hpt or hggt. For example, see WO 02/42424, WO 98/22604, WO 03/011015, WO02/057439, WO03/011015, U.S. Pat. Nos. 6,423,886, 6,197,561, 6,825,397, and U.S. Application Serial Nos. US2003/0079247, US2003/0204870, and Rivera-Madrid, R. et al. Proc. Natl. Acad. Sci. 92:5620-5624 (1995).

B) Altered phosphorus content, for example, by the (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 05/113778 and/or by altering inositol kinase activity as in WO 02/059324, US2003/0009011, WO 03/027243, US2003/0079247, WO 99/05298, U.S. Pat. No. 6,197,561, U.S. Pat. No. 6,291,224, U.S. Pat. No. 6,391,348, WO2002/059324, US2003/0079247, Wo98/45448, WO99/55882, WO01/04147.

(C) Altered carbohydrates effected, for example, by altering a gene for an enzyme that affects the branching pattern of starch or, a gene altering thioredoxin such as NTR and/or TRX (see. (See U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Molec. Biol. 21: 515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac—PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821 which are hereby incorporated by reference. Other systems that may be used include the Gin recombinase of phage Mu (Maeser et al., 1991; Vicki Chandler, *The Maize Handbook ch.* 118 (Springer-Verlag 1994), the Pin recombinase of *E. coli* (Enomoto et al., 1983), and the R/RS system of the pSRi plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), and WO2004076638 and WO2004031349 (transcription factors).

Using 10124870 to Develop Another Maize Plant

The development of maize hybrids in a maize plant breeding program requires, in general, the development of homozygous inbred lines, the crossing of these lines, and the evaluation of the crosses. Maize plant breeding programs combine the genetic backgrounds from two or more inbred varieties or various other germplasm sources into breeding populations from which new inbred varieties are developed by selfing and selection of desired phenotypes. Hybrids also can be used as a source of plant breeding material or as source populations from which to develop or derive new maize varieties. Plant breeding techniques known in the art and used in a maize plant breeding program include, but are not limited to, recurrent selection, mass selection, bulk selection, backcrossing, making double haploids, pedigree breeding, open pollination breeding, restriction fragment length polymorphism enhanced selection, genetic marker enhanced selection, and transformation. Often combinations of these techniques are used. The inbred varieties derived from hybrids can be developed using plant breeding techniques as described above. New inbreds are crossed with other inbred varieties and the hybrids from these crosses are evaluated to determine which of those have commercial potential. The oldest and most traditional method of analysis is the observation of phenotypic traits but genotypic analysis may also be used. Descriptions of breeding methods can also be found in one of several reference books (e.g., Allard, *Principles of Plant Breeding,* 1960; Simmonds, *Principles of Crop Improvement,* 1979; Fehr, "Breeding Methods for Cultivar Development", *Production and Uses,* $2^{nd}$ ed., Wilcox editor, 1987).

Recurrent Selection and Mass Selection

Recurrent selection is a method used in a plant breeding program to improve a population of plants. 10124870 is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and toperossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred varieties to be used in hybrids or used as parents for a synthetic cultivar. A synthetic cultivar is the resultant progeny formed by the intercrossing of several selected inbreds.

10124870 is suitable for use in mass selection. Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Production of Double Haploids

The production of double haploids from 10124870 can also be used for the development of inbreds. Double haploids are produced by the doubling of a set of chromosomes (1N) from a heterozygous plant to produce a completely homozygous individual. For example, a further embodiment of this invention is the method of obtaining a substantially homozygous 10124870 progeny plant by obtaining a seed from the cross of 10124870 and another maize plant and applying double haploid methods to the F1 seed or F1 plant or to any successive filial generation. Such methods substantially decrease the number of generations required to produce an inbred with similar genetics or characteristics to 10124870. For example, see Wan et al., "Efficient Production of Doubled Haploid Plants Through Colchicine Treatment of Anther-Derived Maize Callus", Theoretical and Applied Genetics, 77:889-892, 1989 and U.S. Patent Application 2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected variety (as female) with an inducer variety. Such inducer varieties for maize include Stock 6 (Coe, 1959, *Am. Nat.* 93:381-382; Sharkar and Coe, 1966, *Genetics* 54:453-464) RWS (see the World Wide Web at uni-hohenheim.de/%7Eipspwww/350b/indexe.html#Project3), KEMS (Deimling, Roeber, and Geiger, 1997, *Vortr. Pflanzenzuchtg* 38:203-224), or KMS and ZMS (Chalyk, Bylich & Chebotar, 1994, *MNL* 68:47; Chalyk & Chebotar, 2000, *Plant Breeding* 119:363-364), and indeterminate gametophyte (ig) mutation (Kermicle 1969 *Science* 166:1422-1424), the disclosures of which are incorporated herein by reference.

Methods for obtaining haploid plants are also disclosed in Kobayashi, M. et al., *Journ. of Heredity* 71(1):9-14, 1980, Pollacsek, M., Agronomie (Paris) 12(3):247-251, 1992; Cho-Un-Haing et al., *Journ. of Plant Biol.,* 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, *Maize Genet. Coop. Newsletter* 73:53-54; Coe, R. H., 1959, *Am. Nat.* 93:381-382; Deimling, S. et al., 1997, *Vortr. Pflanzenzuchtg* 38:203-204; Kato, A., 1999, *J. Hered.* 90:276-280; Lashermes, P. et al., 1988, *Theor. Appl. Genet.* 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, *Indian J. Genet Plant Breed* 38:452-457; Chalyk S. T., 1994, Euphytica 79:13-18; Chase, S. S., 1952, *Agron. J.* 44:263-267; Coe, E. H., 1959, *Am. Nat.* 93:381-382; Coe, E. H., and Sarkar, K. R., 1964 *J. Hered.* 55:231-233; Greenblatt, I. M. and Bock, M., 1967, *J. Hered.* 58:9-13; Kato, A., 1990, *Maize Genet. Coop. Newsletter* 65:109-110; Kato, A., 1997, *Sex. Plant Reprod.* 10:96-100; Nanda, D. K. and Chase, S. S., 1966, *Crop Sci.* 6:213-215; Sarkar, K. R. and Coe, E. H., 1966, *Genetics* 54:453-464; Sarkar, K. R. and Coe, E. H., 1971, *Crop Sci.* 11:543-544; Sarkar, K. R. and Sachan J. K. S., 1972, *Indian J. Agric. Sci.* 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; U.S. Pat. No. 5,639,951 and U.S. patent application Ser. No. 10/121,200, the disclosures of which are incorporated herein by reference.

Use Of 10124870 in Tissue Culture

This invention is also directed to the use of maize variety 10124870 in tissue culture. As used herein, the term "tissue culture" includes plant protoplasts, plant cell tissue culture, cultured microspores, plant calli, plant clumps, and the like. As used herein, phrases such as "growing the seed" or "grown from the seed" include embryo rescue, isolation of cells from seed for use in tissue culture, as well as traditional growing methods.

Duncan, Williams, Zehr, and Widholm, *Planta*, (1985) 165:322-332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in *Plant Cell Reports* (1988), 7:262-265 reports several media additions which enhance regenerability of callus of two inbred varieties. Other published reports also indicated that "nontraditional" tissues are capable of producing somatic embryogenesis and plant regeneration. K. P. Rao, et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize, including tassel/anther culture, is described in U.S. Application 2002/0062506A1 and European Patent Application, Publication EP0160,390, each of which are incorporated herein by reference for this purpose. Maize tissue culture procedures are also described in Green and Rhodes, "Plant Regeneration in Tissue Culture of Maize," *Maize for Biological Research* (Plant Molecular Biology Association, Charlottesville, Va. 1982, at 367-372) and in Duncan, et al., "The Production of Callus Capable of Plant Regeneration from Immature Embryos of Numerous *Zea Mays* Genotypes," 165 *Planta* 322-332 (1985). Thus, another aspect of this invention is to provide cells which upon growth and differentiation produce maize plants having the genotype and/or phenotypic characteristics of maize variety 10124870.

INDUSTRIAL APPLICABILITY

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of the maize variety, the plant produced from the seed, a plant produced from crossing of maize variety 10124870 and various parts of the maize plant and transgenic versions of the foregoing, can be utilized for human food, livestock feed, and as a raw material in industry.

TABLE 1

VARIETY DESCRIPTION INFORMATION
10124870 wherein 10124870 comprises locus conversions for a *Bacillus thuringiensis* source of insect resistance, glyphosate resistance and glufosinate resistance

| | | | | |
|---|---|---|---|---|
| 1. | TYPE: (Describe intermediate types in comments section) | AVG | STDEV | N |
| | 1 = Sweet, 2 = Dent, 3 = Flint, 4 = Flour, 5 = Pop and 6 = Ornamental. | 3 | | |
| | Comments: Flint-Dent | | | |
| 2. | MATURITY: DAYS HEAT UNITS | Days | H. Units | |
| | Emergence to 50% of plants in silk | 58 | 1,265 | |
| | Emergence to 50% of plants in pollen shed | 59 | 1,277 | |
| | 10% to 90% pollen shed | 2 | 46 | |
| 3. | PLANT: | | | |
| | Plant Height (to tassel tip) (cm) | 311.2 | 4.29 | 10 |
| | Ear Height (to base of top ear node) (cm) | 128.7 | 11.56 | 10 |
| | Length of Top Ear Internode (cm) | 19.8 | 1.14 | 10 |
| | Average Number of Tillers per Plant | 0.0 | | 1 |
| | Average Number of Ears per Stalk | 1.1 | 0.01 | 2 |
| | Anthocyanin of Brace Roots: 1 = Absent, 2 = Faint, 3 = Moderate, 4 = Dark | 3 | | |
| 4. | LEAF: | | | |
| | Width of Ear Node Leaf (cm) | 10.8 | 0.42 | 10 |
| | Length of Ear Node Leaf (cm) | 89.5 | 3.27 | 10 |
| | Number of Leaves above Top Ear | 6.5 | 0.53 | 10 |
| | Leaf Angle: (at anthesis, 2nd leaf above ear to stalk above leaf) (Degrees) | 26.0 | 5.16 | 10 |
| * | Leaf Color: V. Dark Green Munsell: 7.5GY34 | | | |
| | Leaf Sheath Pubescence: 1 = none to 9 = like peach fuzz | 5 | | |
| 5. | TASSEL: | | | |
| | Number of Primary Lateral Branches | 6.4 | 1.35 | 10 |
| | Branch Angle from Central Spike (Degrees) | 36.0 | 7.38 | 10 |
| | Tassel Length: (from peduncle node to tassel tip), (cm). | 58.1 | 4.93 | 10 |
| | Pollen Shed: 0 = male sterile, 9 = heavy shed | 5 | | |
| * | Anther Color: Red Munsell: 10R38 | | | |
| * | Glume Color: Dark Green Munsell: 5GY46 | | | |
| | Bar Glumes (glume bands): 1 = absent, 2 = present | 1 | | |
| | Peduncle Length: (from top leaf node to lower florets or branches), (cm). | 24.1 | 2.85 | 10 |
| 6a. | EAR (Unhusked ear) | | | |
| * | Silk color: Light Green Munsell: 2.5GY86 (3 days after silk emergence) | | | |
| * | Fresh husk color: Med. Green Munsell: 5GY78 | | | |
| * | Dry husk color: Buff Munsell: 10YR84 (65 days after 50% silking) | | | |
| | Ear position at dry husk stage: 1 = upright, 2 = horizontal, 3 = pendant | 3 | | |
| | Husk Tightness: (1 = very loose, 9 = very tight) | 3 | | |
| | Husk Extension (at harvest): 1 = short (ears exposed), 2 = medium (<8 cm), 3 = long (8-10 cm), 4 = v. long (>10 cm) | 2 | | |
| 6b. | EAR (Husked ear data) | | | |
| | Ear Length (cm): | 18.5 | 1.35 | 10 |
| | Ear Diameter at mid-point (mm) | 49.9 | 1.10 | 10 |
| | Ear Weight (gm): | 241.6 | 25.39 | 10 |
| | Number of Kernel Rows: | 16.4 | 1.84 | 10 |
| | Kernel Rows: 1 = indistinct, 2 = distinct | 2 | | |
| | Row Alignment: 1 = straight, 2 = slightly curved, 3 = spiral | 2 | | |
| | Shank Length (cm): | 9.5 | 1.58 | 10 |
| | Ear Taper: 1 = slight cylind., 2 = average, 3 = extreme conic. | 2 | | |

TABLE 1-continued

VARIETY DESCRIPTION INFORMATION
10124870 wherein 10124870 comprises locus conversions for a *Bacillus thuringiensis* source of insect resistance, glyphosate resistance and glufosinate resistance

| | | | | |
|---|---|---|---|---|
| 7. | KERNEL (Dried): | | | |
| | Kernel Length (mm): | 13.9 | 0.57 | 10 |
| | Kernel Width (mm): | 8.2 | 0.63 | 10 |
| | Kernel Thickness (mm): | 4.0 | 0.00 | 10 |
| | Round Kernels (shape grade) (%) | 17.3 | 4.50 | 2 |
| | Aleurone Color Pattern: 1 = homozygous, 2 = segregating | 1 | | |
| * | Aleurone Color: Yellow Munsell: 10YR814 | | | |
| * | Hard Endo. Color: Yellow Munsell: 10YR712 | | | |
| | Endosperm Type: | 3 | | |
| | 1 = sweet (su1), 2 = extra sweet (sh2), 3 = normal starch, 4 = high amylose starch, 5 = waxy starch, 6 = high protein, 7 = high lysine, 8 = super sweet (se), 9 = high oil, 10 = other | | | |
| | Weight per 100 Kernels (unsized sample) (gm): | 36.1 | 4.38 | 2 |
| 8. | COB: | | | |
| | Cob Diameter at mid-point (mm): | 22.1 | 1.20 | 10 |
| * | Cob Color: Red Munsell: 10R38 | | | |
| 9. | DISEASE RESISTANCE: | | | |
| | (Rate from 1 = most-susceptible to 9 = most-resistant. Leave blank if not tested, leave race or strain options blank if polygenic.) | | | |
| A. | LEAF BLIGHTS, WILTS, AND LOCAL INFECTION DISEASES | | | |
| | Anthracnose Leaf Blight (*Colletotrichum graminicola*) | | | |
| | Common Rust (*Puccinia sorghi*) | | | |
| | 8 Common Smut (*Ustilago maydis*) | | | |
| | Eyespot (*Kabatiella zeae*) | | | |
| | 8 Goss's Wilt (*Clavibacter michiganense* spp. *nebraskense*) | | | |
| | 6 Gray Leaf Spot (*Cercospora zeae-maydis*) | | | |
| | *Helminthosporium* Leaf Spot (*Bipolaris zeicola*) Race: | | | |
| | 6 Northern Leaf Blight (*Exserohilum turcicum*) Race: | | | |
| | 4 Southern Leaf Blight (*Bipolaris maydis*) Race: | | | |
| | Southern Rust (*Puccinia polysora*) | | | |
| | Stewart's Wilt (*Erwinia stewartii*) | | | |
| | Other (Specify): ___________________ | | | |
| B. | SYSTEMIC DISEASES | | | |
| | Corn Lethal Necrosis (MCMV and MDMV) | | | |
| | 6 Head Smut (*Sphacelotheca reiliana*) | | | |
| | Maize Chlorotic Dwarf Virus (MDV) | | | |
| | Maize Chlorotic Mottle Virus (MCMV) | | | |
| | Maize Dwarf Mosaic Virus (MDMV) | | | |
| | *Sorghum* Downy Mildew of Corn (*Peronosclerospora sorghi*) | | | |
| | Other (Specify): ___________________ | | | |
| C. | STALK ROTS | | | |
| | 4 Anthracnose Stalk Rot (*Colletotrichum graminicola*) | | | |
| | *Diplodia* Stalk Rot (*Stenocarpella maydis*) | | | |
| | *Fusarium* Stalk Rot (*Fusarium moniliforme*) | | | |
| | *Gibberella* Stalk Rot (*Gibberella zeae*) | | | |
| | Other (Specify): ___________________ | | | |
| D. | EAR AND KERNEL ROTS | | | |
| | *Aspergillus* Ear and Kernel Rot (*Aspergillus flavus*) | | | |
| | 7 *Diplodia* Ear Rot (*Stenocarpella maydis*) | | | |
| | 5 *Fusarium* Ear and Kernel Rot (*Fusarium moniliforme*) | | | |
| | *Gibberella* Ear Rot (*Gibberella zeae*) | | | |
| | Other (Specify): ___________________ | | | |
| 10. | INSECT RESISTANCE: | | | |
| | (Rate from 1 = most-suscept. to 9 = most-resist., leave blank if not tested.) | | | |
| | Corn Worm (*Helicoverpa zea*) | | | |
| | ___ Leaf Feeding | | | |
| | ___ Silk Feeding | | | |
| | ___ Ear Damage | | | |
| | Corn Leaf Aphid (*Rophalosiphum maydis*) | | | |
| | Corn Sap Beetle (*Capophilus dimidiatus*) | | | |
| | European Corn Borer (*Ostrinia nubilalis*) | | | |
| | 1st. Generation (Typically whorl leaf feeding) | | | |
| | 2nd. Generation (Typically leaf sheath-collar feeding) | | | |
| | ___ Stalk Tunneling | | | |
| | ___ cm tunneled/plant | | | |
| | Fall armyworm (*Spodoptera fruqiperda*) | | | |
| | ___ Leaf Feeding | | | |
| | ___ Silk Feeding | | | |
| | ___ mg larval wt. | | | |
| | Maize Weevil (*Sitophilus zeamaize*) | | | |
| | Northern Rootworm (*Diabrotica barberi*) | | | |
| | Southern Rootworm (*Diabrotica undecimpunctata*) | | | |
| | Southwestern Corn Borer (*Diatreaea grandiosella*) | | | |
| | ___ Leaf Feeding | | | |
| | ___ Stalk Tunneling | | | |
| | ___ cm tunneled/plant | | | |

TABLE 1-continued

VARIETY DESCRIPTION INFORMATION
10124870 wherein 10124870 comprises locus conversions for a *Bacillus thuringiensis* source of insect resistance, glyphosate resistance and glufosinate resistance

| | |
|---|---|
| | Two-spotted Spider Mite (*Tetranychus utricae*) |
| | Western Rootworm (*Diabrotica virgifrea virgifrea*) |
| | Other (Specify): ___________________ |
| 11. | AGRONOMIC TRAITS: |
| 4 | Staygreen (at 65 days after anthesis; rate from 1-worst to 9-excellent) |
| | % Dropped Ears (at 65 days after anthesis) |
| | % Pre-anthesis Brittle Snapping |
| 42 | % Pre-anthesis Root Lodging |
| 8 | % Post-anthesis Root Lodging (at 65 days after anthesis) |
| | % Post-anthesis Stalk Lodging |
| 13,159.0 | Kg/ha (Yield at 12-13% grain moisture) |

* Munsell Glossy Book of color, (A standard color reference). Kollmorgen Inst. Corp. New Windsor, NY.

TABLE 2A

HYBRID COMPARISON
Variety #1: 10124870 wherein 10124870 comprises locus conversions for a *Bacillus thuringiensis* source of insect resistance, glyphosate resistance and glufosinate resistance
Variety #2: 33D11

| Stat | YIELD BU/A 56# ABS | GLFSPT SCORE ABS | YIELD BU/A 56# % MN | NLFBLT SCORE ABS | SLFBLT SCORE ABS | MST PCT ABS | TSTWT LB/BU ABS | ANTROT SCORE ABS | ESTCNT COUNT ABS |
|---|---|---|---|---|---|---|---|---|---|
| Mean1 | 210.4 | 5.5 | 103.8 | 5.6 | 4.5 | 20.8 | 57.3 | 4.2 | 63.0 |
| Mean2 | 198.1 | 3.9 | 98.2 | 4.5 | 2.5 | 20.2 | 56.8 | 3.0 | 59.0 |
| Locs | 63 | 4 | 63 | 4 | 1 | 63 | 37 | 3 | 1 |
| Reps | 71 | 6 | 71 | 7 | 2 | 71 | 42 | 6 | 2 |
| Diff | 12.3 | 1.6 | 5.6 | 1.1 | 2.0 | −0.6 | 0.5 | 1.2 | 4.0 |
| Prob | 0.000 | 0.051 | 0.000 | 0.547 | . | 0.014 | 0.110 | 0.020 | . |

| Stat | STKCNT COUNT ABS | DIPERS SCORE ABS | GDUSHD GDU ABS | GDUSLK GDU ABS | PLTHT CM ABS | EARHT CM ABS | STAGRN SCORE ABS | GIBROT SCORE ABS | HDSMT % NOT ABS |
|---|---|---|---|---|---|---|---|---|---|
| Mean1 | 55.8 | 6.8 | 133.8 | 133.3 | 318.5 | 129.3 | 4.4 | 7.5 | 95.0 |
| Mean2 | 55.4 | 5.5 | 130.8 | 130.4 | 302.4 | 125.9 | 3.3 | 6.0 | 91.7 |
| Locs | 103 | 3 | 8 | 11 | 27 | 27 | 24 | 1 | 2 |
| Reps | 176 | 6 | 8 | 11 | 36 | 36 | 26 | 2 | 6 |
| Diff | 0.4 | 1.3 | 3.0 | 2.9 | 16.1 | 3.4 | 1.1 | 1.5 | 3.3 |
| Prob | 0.061 | 0.251 | 0.013 | 0.022 | 0.000 | 0.129 | 0.000 | . | 0.531 |

| Stat | STLLPN % NOT ABS | STLPCN % NOT ABS | ERTLPN % NOT ABS | LRTLPN % NOT ABS | BRLPNE PCTNOT ABS | BRTSTK % NOT ABS | HSKCVR SCORE ABS |
|---|---|---|---|---|---|---|---|
| Mean1 | 74.1 | 92.5 | 85.0 | 95.6 | 81.0 | 97.0 | 6.5 |
| Mean2 | 58.4 | 60.0 | 95.0 | 83.3 | 41.8 | 100.0 | 6.0 |
| Locs | 10 | 4 | 1 | 9 | 2 | 1 | 6 |
| Reps | 18 | 4 | 2 | 12 | 9 | 1 | 6 |
| Diff | 15.7 | 32.5 | −10.0 | 12.2 | 39.2 | −3.0 | 0.5 |
| Prob | 0.025 | 0.090 | . | 0.127 | 0.152 | . | 0.296 |

TABLE 2B

HYBRID COMPARISON
Variety #1: 10124870 wherein 10124870 comprises locus conversions for a *Bacillus thuringiensis* source of insect resistance, glyphosate resistance and glufosinate resistance
Variety #2: 33M14

| Stat | YIELD BU/A 56# ABS | GLFSPT SCORE ABS | YIELD BU/A 56# % MN | NLFBLT SCORE ABS | SLFBLT SCORE ABS | MST PCT ABS | TSTWT LB/BU ABS | ANTROT SCORE ABS |
|---|---|---|---|---|---|---|---|---|
| Mean1 | 209.5 | 5.5 | 103.8 | 5.6 | 4.5 | 20.8 | 57.4 | 4.2 |
| Mean2 | 198.2 | 6.0 | 98.5 | 2.4 | 4.5 | 20.2 | 57.0 | 2.9 |
| Locs | 61 | 4 | 61 | 4 | 1 | 62 | 36 | 3 |

TABLE 2B-continued

HYBRID COMPARISON
Variety #1: 10124870 wherein 10124870 comprises locus conversions for a *Bacillus thuringiensis* source of insect resistance, glyphosate resistance and glufosinate resistance
Variety #2: 33M14

| | | | | | | | | |
|---|---|---|---|---|---|---|---|---|
| Reps | 69 | 7 | 69 | 7 | 2 | 71 | 41 | 6 |
| Diff | 11.3 | −0.5 | 5.3 | 3.3 | 0.0 | −0.6 | 0.3 | 1.3 |
| Prob | 0.000 | 0.252 | 0.001 | 0.044 | . | 0.001 | 0.235 | 0.013 |

| Stat | FUSERS SCORE ABS | STKCNT COUNT ABS | DIPERS SCORE ABS | GDUSHD GDU ABS | GDUSLK GDU ABS | PLTHT CM ABS | EARHT CM ABS | STAGRN SCORE ABS |
|---|---|---|---|---|---|---|---|---|
| Mean1 | 4.4 | 54.1 | 6.8 | 135.2 | 135.3 | 325.6 | 133.3 | 4.4 |
| Mean2 | 5.4 | 54.1 | 4.5 | 131.6 | 130.6 | 298.9 | 117.0 | 4.9 |
| Locs | 3 | 85 | 3 | 9 | 12 | 19 | 19 | 24 |
| Reps | 8 | 138 | 6 | 10 | 13 | 19 | 19 | 26 |
| Diff | −1.0 | 0.0 | 2.3 | 3.6 | 4.8 | 26.7 | 16.2 | −0.5 |
| Prob | 0.184 | 0.860 | 0.020 | 0.006 | 0.005 | 0.000 | 0.000 | 0.175 |

| Stat | GIBROT SCORE ABS | HDSMT % NOT ABS | STLLPN % NOT ABS | STLPCN % NOT ABS | LRTLPN % NOT ABS | BRLPNE PCTNOT ABS | BRTSTK % NOT ABS | HSKCVR SCORE ABS |
|---|---|---|---|---|---|---|---|---|
| Mean1 | 7.5 | 95.0 | 74.1 | 92.5 | 95.6 | 81.0 | 97.0 | 6.5 |
| Mean2 | 6.5 | 93.6 | 73.4 | 92.5 | 92.6 | 69.2 | 100.0 | 6.0 |
| Locs | 1 | 2 | 10 | 4 | 9 | 2 | 1 | 6 |
| Reps | 2 | 6 | 18 | 4 | 12 | 9 | 1 | 6 |
| Diff | 1.0 | 1.4 | 0.7 | 0.0 | 3.0 | 11.8 | −3.0 | 0.5 |
| Prob | . | 0.490 | 0.848 | 1.000 | 0.402 | 0.482 | . | 0.203 |

TABLE 2C

HYBRID COMPARISON
Variety #1: 10124870 wherein 10124870 comprises locus conversions for a *Bacillus thuringiensis* source of insect resistance, glyphosate resistance and glufosinate resistance
Variety #2: 33T56

| Stat | YIELD BU/A 56# ABS | GLFSPT SCORE ABS | YIELD BU/A 56# % MN | NLFBLT SCORE ABS | SLFBLT SCORE ABS | MST PCT ABS | TSTWT LB/BU ABS | ANTROT SCORE ABS |
|---|---|---|---|---|---|---|---|---|
| Mean1 | 210.4 | 5.5 | 103.8 | 5.6 | 4.5 | 20.9 | 57.3 | 4.2 |
| Mean2 | 202.3 | 4.6 | 100.4 | 5.0 | 3.0 | 20.3 | 56.4 | 2.9 |
| Locs | 63 | 4 | 63 | 4 | 1 | 64 | 37 | 3 |
| Reps | 71 | 7 | 71 | 7 | 2 | 73 | 42 | 6 |
| Diff | 8.1 | 0.9 | 3.4 | 0.6 | 1.5 | −0.6 | 0.9 | 1.3 |
| Prob | 0.008 | 0.235 | 0.049 | 0.638 | . | 0.004 | 0.010 | 0.013 |

| Stat | FUSERS SCORE ABS | STKCNT COUNT ABS | DIPERS SCORE ABS | GDUSHD GDU ABS | GDUSLK GDU ABS | PLTHT CM ABS | EARHT CM ABS | STAGRN SCORE ABS |
|---|---|---|---|---|---|---|---|---|
| Mean1 | 4.4 | 54.2 | 6.8 | 135.2 | 135.3 | 325.6 | 133.3 | 4.4 |
| Mean2 | 4.9 | 54.1 | 6.0 | 129.9 | 132.6 | 309.4 | 129.9 | 4.1 |
| Locs | 3 | 86 | 3 | 9 | 12 | 19 | 19 | 24 |
| Reps | 8 | 140 | 6 | 10 | 13 | 19 | 19 | 26 |
| Diff | −0.5 | 0.1 | 0.8 | 5.3 | 2.8 | 16.2 | 3.3 | 0.3 |
| Prob | 0.478 | 0.635 | 0.444 | 0.002 | 0.014 | 0.000 | 0.190 | 0.303 |

| Stat | GIBROT SCORE ABS | HDSMT %NOT ABS | STLLPN % NOT ABS | STLPCN % NOT ABS | LRTLPN % NOT ABS | BRLPNE PCTNOT ABS | BRTSTK % NOT ABS | HSKCVR SCORE ABS |
|---|---|---|---|---|---|---|---|---|
| Mean1 | 7.5 | 95.0 | 74.1 | 92.5 | 95.6 | 81.0 | 97.0 | 6.5 |
| Mean2 | 5.0 | 93.9 | 77.3 | 87.5 | 80.1 | 43.5 | 87.7 | 6.7 |
| Locs | 1 | 2 | 10 | 4 | 9 | 2 | 1 | 6 |
| Reps | 2 | 6 | 18 | 4 | 12 | 10 | 1 | 6 |
| Diff | 2.5 | 1.2 | −3.3 | 5.0 | 15.4 | 37.5 | 9.3 | −0.2 |
| Prob | . | 0.340 | 0.641 | 0.391 | 0.136 | 0.082 | . | 0.695 |

TABLE 2D

HYBRID COMPARISON
Variety #1: 10124870 wherein 10124870 comprises locus conversions for a *Bacillus thuringiensis* source of insect resistance, glyphosate resistance and glufosinate resistance
Variety #2: X7K444

| Stat | YIELD BU/A 56# ABS | GLFSPT SCORE ABS | YIELD BU/A 56# % MN | NLFBLT SCORE ABS | SLFBLT SCORE ABS | MST PCT ABS | TSTWT LB/BU ABS | ANTROT SCORE ABS |
|---|---|---|---|---|---|---|---|---|
| Mean1 | 210.0 | 5.5 | 103.3 | 5.6 | 4.5 | 20.9 | 57.3 | 4.2 |
| Mean2 | 208.6 | 5.5 | 102.4 | 5.9 | 3.0 | 19.4 | 58.2 | 3.0 |
| Locs | 60 | 4 | 60 | 4 | 1 | 62 | 37 | 3 |
| Reps | 67 | 7 | 67 | 7 | 2 | 70 | 41 | 6 |
| Diff | 1.4 | 0.0 | 0.9 | −0.3 | 1.5 | −1.5 | −0.8 | 1.2 |
| Prob | 0.565 | 1.000 | 0.443 | 0.182 | . | 0.000 | 0.006 | 0.020 |

| Stat | FUSERS SCORE ABS | STKCNT COUNT ABS | DIPERS SCORE ABS | GDUSHD GDU ABS | GDUSLK GDU ABS | PLTHT CM ABS | EARHT CM ABS | STAGRN SCORE ABS |
|---|---|---|---|---|---|---|---|---|
| Mean1 | 4.4 | 54.2 | 6.8 | 135.2 | 135.3 | 325.6 | 133.3 | 4.4 |
| Mean2 | 4.8 | 54.0 | 5.3 | 131.6 | 131.3 | 307.4 | 122.2 | 3.7 |
| Locs | 3 | 84 | 3 | 9 | 12 | 19 | 19 | 24 |
| Reps | 8 | 137 | 6 | 10 | 13 | 19 | 19 | 26 |
| Diff | −0.3 | 0.2 | 1.5 | 3.6 | 4.0 | 18.2 | 11.1 | 0.8 |
| Prob | 0.184 | 0.301 | 0.096 | 0.012 | 0.002 | 0.000 | 0.000 | 0.011 |

| Stat | GIBROT SCORE ABS | HDSMT % NOT ABS | STLLPN % NOT ABS | STLPCN % NOT ABS | LRTLPN % NOT ABS | BRLPNE PCTNOT ABS | BRTSTK % NOT ABS | HSKCVR SCORE ABS |
|---|---|---|---|---|---|---|---|---|
| Mean1 | 7.5 | 95.0 | 74.1 | 92.5 | 95.6 | 81.0 | 97.0 | 6.5 |
| Mean2 | 5.0 | 93.2 | 82.3 | 97.5 | 92.2 | 79.3 | 97.0 | 6.0 |
| Locs | 1 | 2 | 10 | 4 | 9 | 2 | 1 | 6 |
| Reps | 2 | 6 | 18 | 4 | 12 | 10 | 1 | 6 |
| Diff | 2.5 | 1.8 | −8.3 | −5.0 | 3.3 | 1.7 | 0.0 | 0.5 |
| Prob | . | 0.734 | 0.217 | 0.182 | 0.397 | 0.315 | . | 0.076 |

Deposits

Applicant(s) have made a deposit of at least 2500 seeds of parental maize inbred varieties PHGMA and PHNWJ with the American Type Culture Collection (ATCC), 10801 University Boulevard, Manassas, Va. 20110 USA, ATCC Deposit Nos. PTA-11179 and PTA-9934, respectively. The seeds deposited with the ATCC on Jul. 12, 2010 for PTA-11179 and on Apr. 2, 2009 for PTA-9934, respectively were taken from the seed stock maintained by Pioneer Hi-Bred International, Inc., 7250 NW 62$^{nd}$ Avenue, Johnston, Iowa 50131-1000 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit of at least 2500 seeds of parental maize inbred varieties PHGMA and PHNWJ with the American Type Culture Collection (ATCC), 10801 University Boulevard, Manassas, Va. 20110-2209. This deposits of the seed of parental maize inbred varieties for Maize Variety 10124870 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have or will satisfy all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to Maize Variety 10124870 and/or its parental maize inbred varieties PHGMA and PHNWJ under either the patent laws or the Plant Variety Protection Act (7 USC 2321 et seq.). U.S. Plant Variety Protection of parental maize inbred varieties PHGMA and PHNWJ has been applied for and may have issued. Unauthorized seed multiplication is prohibited.

REFERENCES

The following references, to the extent that they provide exemplary procedural or other details supplementary to those set forth herein, are specifically incorporated by reference.

Aukerman, M. J. et al. (2003) "Regulation of Flowering Time and Floral Organ Identity by a MicroRNA and Its APETALA2-like Target Genes" *The Plant Cell* 15:2730-2741

Berry et al., "Assessing Probability of Ancestry Using Simple Sequence Repeat Profiles: Applications to Maize Hybrids and Inbreds", Genetics 161:813-824 (2002)

Berry et al., "Assessing Probability of Ancestry Using Simple Sequence Repeat Profiles: Applications to Maize Inbred Lines and Soybean Varieties" Genetics 165:331-342 (2003)

Boppenmaier, et al., "Comparisons Among Strains of Inbreds for RFLPs", Maize Genetics Cooperative Newsletter, 65:1991, p. 90

Conger, B. V., et al. (1987) "Somatic Embryogenesis From Cultured Leaf Segments of *Zea Mays", Plant Cell Reports,* 6:345-347

Duncan, D. R., et al. (1985) "The Production of Callus Capable of Plant Regeneration From Immature Embryos of Numerous *Zea Mays* Genotypes", *Planta,* 165:322-332

Edallo, et al. (1981) "Chromosomal Variation and Frequency of Spontaneous Mutation Associated with in Vitro Culture and Plant Regeneration in Maize", *Maydica*, XXVI: 39-56

Fehr, Walt, Principles of Cultivar Development, pages 261-286 (1987)

Green, et al. (1975) "Plant Regeneration From Tissue Cultures of Maize", *Crop Science*, Vol. 15, pages 417-421

Green, C. E., et al. (1982) "Plant Regeneration in Tissue Cultures of Maize" *Maize for Biological Research*, pages 367-372

Hallauer, A. R. et al. (1988) "Corn Breeding" *Corn and Corn Improvement*, No. 18, pages 463-481

Lee, Michael (1994) "Inbred Lines of Maize and Their Molecular Markers", *The Maize Handbook*, Ch. 65:423-432

Meghji, M. R., et al. (1984) "Inbreeding Depression, Inbred & Hybrid Grain Yields, and Other Traits of Maize Genotypes Representing Three Eras", *Crop Science*, Vol. 24, pages 545-549

Openshaw, S. J., et al. (1994) "Marker-assisted selection in backcross breeding", pages 41-43. In Proceedings of the Symposium Analysis of Molecular Marker Data. 5-7 Aug. 1994. Corvallis, Oreg., American Society for Horticultural Science/Crop Science Society of America Phillips, et al. (1988) "Cell/Tissue Culture and In Vitro Manipulation", *Corn & Corn Improvement,* 3rd Ed., ASA Publication, No. 18, pages 345-387

Poehlman et al. (1995) *Breeding Field Crop,* 4th Ed., Iowa State University Press, Ames, Iowa., pages 132-155 and 321-344

Rao, K. V., et al., (1986) "Somatic Embryogenesis in Glume Callus Cultures", *Maize Genetics Cooperative Newsletter*, No. 60, pages 64-65

Sass, John F. (1977) "Morphology", *Corn & Corn Improvement*, ASA Publication, Madison, Wis. pages 89-109

Smith, J. S. C., et al., "The Identification of Female Selfs in Hybrid Maize: A Comparison Using Electrophoresis and Morphology", Seed Science and Technology 14, 1-8

Songstad, D. D. et al. (1988) "Effect of ACC (1-aminocyclopropane-1-carboyclic acid), Silver Nitrate & Norbonadiene on Plant Regeneration From Maize Callus Cultures", *Plant Cell Reports,* 7:262-265

Tomes, et al. (1985) "The Effect of Parental Genotype on Initiation of Embryogenic Callus From Elite Maize (*Zea Mays* L.) Germplasm", *Theor. Appl. Genet.*, Vol. 70, p. 505-509

Troyer, et al. (1985) "Selection for Early Flowering in Corn: 10 Late Synthetics", *Crop Science*, Vol. 25, pages 695-697

Umbeck, et al. (1983) "Reversion of Male-Sterile T-Cytoplasm Maize to Male Fertility in Tissue Culture", *Crop Science*, Vol. 23, pages 584-588

Wan et al., "Efficient Production of Doubled Haploid Plants Through Colchicine Treatment of Anther-Derived Maize Callus", Theoretical and Applied Genetics, 77:889-892, 1989

Wright, Harold (1980) "Commercial Hybrid Seed Production", *Hybridization of Crop Plants*, Ch. 8:161-176

Wych, Robert D. (1988) "Production of Hybrid Seed", *Corn and Corn Improvement*, Ch. 9, pages 565-607

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A maize variety hybrid 10124870, produced by crossing a first plant of maize variety PHGMA with a second plant of maize variety PHNWJ, wherein representative seed of said maize varieties PHGMA and PHNWJ have been deposited under ATCC Accession Number PTA-11179 and PTA-9934, respectively.

2. A seed of the maize variety of claim 1.

3. A seed of maize variety hybrid 10124870, further comprising a transgenic event.

4. The seed of claim 3, wherein the transgenic event confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

5. A seed of maize variety hybrid 10124870, further comprising a locus conversion, wherein said converted hybrid otherwise has essentially the same phenotypic traits as maize variety hybrid 10124870 listed in Table 1, when grown under the same environmental conditions.

6. The seed of claim 5, wherein the locus conversion confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

7. A plant or plant part of the maize variety of claim 1.

8. A method for producing a second maize plant comprising applying plant breeding techniques to a first maize plant, or parts thereof, wherein said first maize plant is the maize plant of claim 7, and wherein application of said techniques results in the production of said second maize plant.

9. The method of claim 8, further defined as producing an inbred maize plant derived from maize variety hybrid 10124870, the method comprising the steps of:

(a) crossing said first maize plant with itself or another maize plant to produce seed of a subsequent generation;

(b) harvesting and planting the seed of the subsequent generation to produce at least one plant of the subsequent generation;

(c) repeating steps (a) and (b) for an additional 2-10 generations to produce an inbred maize plant derived from maize variety hybrid 10124870.

10. The method of claim 8, further defined as producing an inbred maize plant derived from maize variety hybrid 10124870, the method comprising the steps of:

(a) crossing said first maize plant with an inducer variety to produce haploid seed; and (b) doubling the haploid seed to produce an inbred maize plant derived from maize variety hybrid 10124870.

11. A maize plant grown from the seed of claim 3 or a part of said plant, said plant or plant part comprising said transgenic event.

12. The plant of claim 11, wherein the transgenic event confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

13. A method for producing a second maize plant comprising applying plant breeding techniques to a first maize plant, or parts thereof, wherein said first maize plant is the maize plant of claim 11, and wherein application of said techniques results in the production of said second maize plant.

14. The method of claim 13, further defined as producing an inbred maize plant derived from maize variety hybrid 10124870, the method comprising the steps of:

(a) crossing said first maize plant with itself or another maize plant to produce seed of a subsequent generation;

(b) harvesting and planting the seed of the subsequent generation to produce at least one plant of the subsequent generation;

(c) repeating steps (a) and (b) for an additional 2-10 generations to produce an inbred maize plant derived from maize variety hybrid 10124870.

15. The method of claim 13, further defined as producing an inbred maize plant derived from maize variety hybrid 10124870, the method comprising the steps of:

(a) crossing said first maize plant with an inducer variety to produce haploid seed; and (b) doubling the haploid seed to produce an inbred maize plant derived from maize variety hybrid 10124870.

16. A maize plant grown from the seed of claim 5, or part of, said plant or plant part comprising said locus conversion, wherein said converted hybrid otherwise has essentially the same phenotypic traits as maize variety hybrid 10124870 listed in Table 1, when grown under the same environmental conditions.

17. The plant or plant part of claim 16, wherein the locus conversion confers a trait selected from the group consisting of male sterility, site-specific recombination, abiotic stress tolerance, altered phosphorus, altered antioxidants, altered fatty acids, altered essential amino acids, altered carbohydrates, herbicide resistance, insect resistance and disease resistance.

18. A method for producing a second maize plant comprising applying plant breeding techniques to a first maize plant, or parts thereof, wherein said first maize plant is the maize plant of claim 16, and wherein application of said techniques results in the production of said second maize plant.

19. The method of claim 18, further defined as producing an inbred maize plant derived from maize variety hybrid 10124870, the method comprising the steps of:

(a) crossing said first maize plant with itself or another maize plant to produce seed of a subsequent generation;

(b) harvesting and planting the seed of the subsequent generation to produce at least one plant of the subsequent generation;

(c) repeating steps (a) and (b) for an additional 2-10 generations to produce an inbred maize plant derived from maize variety hybrid 10124870.

20. The method of claim 18, further defined as producing an inbred maize plant derived from maize variety hybrid 10124870, the method comprising the steps of:

(a) crossing said first maize plant with an inducer variety to produce haploid seed; and (b) doubling the haploid seed to produce an inbred maize plant derived from maize variety hybrid 10124870.

* * * * *